United States Patent
Fuchs et al.

(10) Patent No.: US 6,570,058 B1
(45) Date of Patent: May 27, 2003

(54) HIGH LIQUID SUCTION ABSORBENT STRUCTURES

(75) Inventors: Christofer Fuchs, Kronberg (DE); Manfred Plischke, Steinbach/Ts. (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/647,835
(22) PCT Filed: Apr. 16, 1999
(86) PCT No.: PCT/IB99/00689
§ 371 (c)(1),
(2), (4) Date: Oct. 5, 2000
(87) PCT Pub. No.: WO99/53877
PCT Pub. Date: Oct. 28, 1999

(30) Foreign Application Priority Data

Apr. 22, 1998 (EP) ............................................. 98107288

(51) Int. Cl.$^7$ ................................................ A61F 13/15
(52) U.S. Cl. ...................................................... 604/378
(58) Field of Search ................................ 604/367, 368, 604/370, 374, 378, 385.23

(56) References Cited

U.S. PATENT DOCUMENTS

| | | | |
|---|---|---|---|
| 5,562,646 A | * | 10/1996 | Goldman et al. ............ 604/368 |
| 5,599,335 A | * | 2/1997 | Goldman et al. ............ 604/368 |
| 5,669,894 A | * | 9/1997 | Goldman et al. ............ 604/368 |
| 5,895,379 A | * | 4/1999 | Litchholt et al. ............ 604/378 |
| 5,941,862 A | * | 8/1999 | Haynes et al. .............. 604/368 |
| 6,372,952 B1 | * | 4/2002 | Lash et al. .................. 604/369 |
| 6,224,961 B1 | * | 5/2002 | Hsueh et al. .................. 428/72 |

* cited by examiner

Primary Examiner—Weilun Lo
Assistant Examiner—Michael Bogart
(74) Attorney, Agent, or Firm—Edward J. Milbrada; Joan B. Cunningham; Ken K. Patel

(57) ABSTRACT

The present invention is an absorbent structure with an ultimate fluid storage member, comprising superabsorbent material at a relatively high concentration whereby the superabsorbent material has a good Performance under Pressure performance as well as a good Saline Flow conductivity. Further, the absorbent structure comprises a nonwoven wrap sheet comprising small diameter fibers, which is in direct fluid communication with said storage member, and which has low strike-through times in a repeated modified strike through test.

24 Claims, 5 Drawing Sheets

HIGH LIQUID SUCTION ABSORBENT STRUCTURES

GENERAL FIELD OF THE INVENTION

Figure 1:
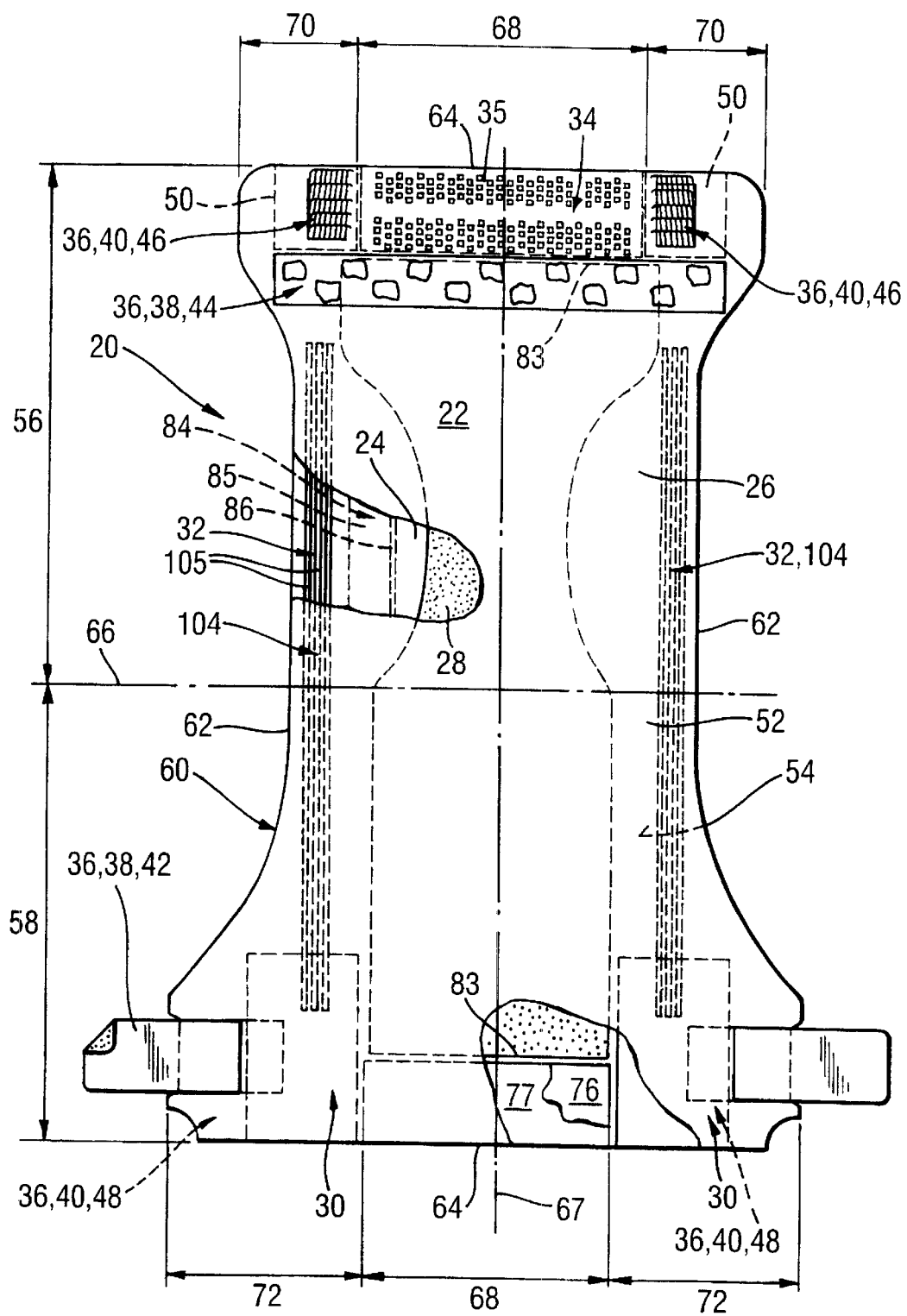

The present invention relates to absorbent structures particularly useful in absorbent hygienic articles, such as baby or adult incontinence diapers, hygienic feminine protection articles and the like.

BACKGROUND/PRIOR ART

Absorbent articles for receiving and retaining bodily discharges such as urine or feces such as disposable diapers, training pants, adult incontinence articles are well known in the art, and significant effort has been spent against improving their performance. The ability to provide better performing absorbent articles such as diapers has been contingent on the ability to develop relatively thin absorbent cores or structures that can acquire and store large quantities of discharged body fluids, in particular urine.

In this regard, the use of certain absorbent polymers often referred to as "hydrogels," "superabsorbents" or "hydrocolloid" or "hydrogel forming" material has been particularly important. See, for example, U.S. Pat. No. 3,699,103 (Harper et al), issued Jun. 13, 1972, and U.S. Pat. No. 3,770,731 (Harmon), issued Jun. 20, 1972, that disclose the use of such absorbent polymers (hereafter "hydrogel-forming absorbent polymers") in absorbent articles. Indeed, the development of thinner diapers has been the direct consequence of thinner absorbent cores that take advantage of the ability of these hydrogel-forming absorbent polymers to absorb large quantities of discharged body fluids, typically when used in combination with a fibrous matrix. See, for example, U.S. Pat. No. 4,673,402 (Weisman et al), issued Jun. 16, 1987 and U.S. Pat. No. 4,935,022 (Lash et al), issued Jun. 19, 1990, that disclose dual-layer core structures comprising a fibrous matrix and hydrogel-forming absorbent polymers useful in fashioning thin, compact, non-bulky diapers. See also, U.S. Pat. No. 5,562,646 (Goldman et al.), issued Oct. 8, 1996 and U.S. Pat. No. 5,599,335 (Goldman et al.), issued Feb. 4, 1997, both of which relate to absorbent cores comprising regions of high concentrations of hydrogel-forming polymer, where the polymer forms a gel-continuous fluid transportation zone upon swelling.

Also the application of such materials in absorbent structures and absorbent articles focused on storage of the fluids within the structure, often considering comfort aspects like thinness of the structure, such as disclosed U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; EP-A-0 640 330 of Bewick-Sonntag et al.; U.S. Pat. No. 5,180,622 (Berg et al.); U.S. Pat. No. 5,102,597 (Roe et al.); U.S. Pat. No. 5,387,207 (LaVon); EP-A-774.242; or EP-A-0.797.968 and EP-A-0.810.078.

With improved liquid handling properties of the absorbent members, their fluid retention and suction ability was increased by two mechanisms, namely the liquid suction of the absorbent materials (such as superabsorbent materials) per se on one side, and on the other side the possibility to use higher amounts and especially higher concentrations of such materials.

Especially with particulate superabsorbent material a further problem was identified, namely the containment of these particles within the absorbent member—in the dry state as well as in the wet state.

Generally, conventional tissue wrap sheets are well known in the art to address this problem. In U.S. Pat. No. 5,458,592 (Abuto), thermoplastic fibrous non-woven core wrap webs are described, aiming at an improvement over paper tissues as well as over conventional nonwoven webs. The benefit over the latter is attributed to the smaller pore size of the described webs, which are exemplified as so-called melt-blown webs. Such webs are essentially made from hydrophobic base materials, such as polyolefins like polypropylene, or are made from other polymeric materials exhibiting an insufficient hydrophilicity. Therefore, surfactants are utilized to improve hydrophilicity, such as of the TRITON X-102 type, which readily washed out However, the prior art, and especially the disclosure of U.S. Pat. No. 5,458,592 (Abuto), failed to recognize, with respect to the fluid handling properties, the interaction which occurs when non-woven core wraps are combined with modern fluid storage members, which have a strong liquid retention ability, and which are designed for uses with multiple gushes. Under such conditions, inventors have realized, that it is not only important that the core wrap non-wovens are sufficiently hydrophilic to allow wetting, but also that the non-wovens must be able to maintain their hydrophilicity for subsequent gushes.

The key effect which makes this an important requirement is the ability of the storage member to dry out the pores of the core wrap materials, such that upon receipt of the subsequent loading or gush, the web performs like a hydrophobic barrier. In case of storage members with a lower dewatering capability, such as the ones disclosed in U.S. Pat. No. 5,458,592 (Abuto), these do not dewater the small pore webs, such as can be achieved by small diameter fiber webs, such that there is still some residual liquid in the pores of the web such that upon rewetting the liquid can readily penetrate there through.

OBJECTS OF THE INVENTION

Henceforth, it is an object of the present invention to provide high suction absorbent structures with a melt-blown non-woven wrap sheet, comprising small diameter fibers, which do not have these drawbacks, and allow good liquid penetration over repeated gushes, without compromising on liquid retention.

SUMMARY

The present invention is an absorbent structure with an ultimate fluid storage member, comprising superabsorbent material at a concentration of at least 40% of the total weight of said ultimate fluid storage member, preferably more than 50%, more preferably more than 60%, and in even more preferred executions more than 70% or even more than 90%, whereby the superabsorbent material has a Performance under pressure (PUP) value of at least 23 g/g, preferably 25 g/g, more preferably more than 29919, and a Saline Flow Conductivity (SFC) value of at least $30 \times 10^{-7}$ cm3 sec/g, preferably more than $50 \times 10^{-7}$ cm3 sec/g, even more preferably more than $100 \times 10^{-7}$ cm3 sec/g. Further, the absorbent structure comprises a non-woven wrap sheet comprising fibers having a diameter corresponding to less than 1.2 dTex, preferably less than 0.9 dTex, and even more preferably less than 0.7 dTex, which is in direct fluid communication with said storage member, and which has in the strike-through test as described hereinafter a strike-through time in the second load of less than 60 seconds, preferably less than 30 seconds, even more preferably of less than 10 seconds, and most preferably less than 5 seconds.

In the absorbent structure, the wrap sheet can completely envelope the absorbent member by being in direct contact with all of the six surfaces of the absorbent member, or only parts of the surface, such that the absorbent structure may also be in direct contact with the backsheet of the article. Also, the absorbent structure can comprise more than one wrap sheets.

The absorbent structure is particularly useful in absorbent articles, such as baby or adult incontinence diapers, optionally in combination with other fluid handling members, such as distribution or acquisition member.

BRIEF DESCRIPTION OF DRAWINGS—TO BE CONFIRMED

FIG. 1—Diaper as example for an absorbent article

FIG. 2—Saline Flow Conductivity Test stand (SFC)

FIG. 3—Performance Under Pressure Test stand (PUP)

DETAILED DESCRIPTION

Definitions

As used herein, the term "absorbent articles" refers to devices which absorb and contain body exudates, and, more specifically, refers to devices which are placed against or in proximity to the body of the wearer to absorb and contain the various exudates discharged from the body. As used herein, the term "body fluids" includes, but is not limited to, urine, menses and vaginal discharges, sweat and feces.

The term "disposable" is used herein to describe absorbent articles which are not intended to be laundered or otherwise restored or reused as an absorbent article (i.e., they are intended to be discarded after use and, preferably, to be recycled, composted or otherwise disposed of in an environmentally compatible manner).

As used herein, the term "Z-dimension" refers to the dimension orthogonal to the length and width of the member, core or article. The Z-dimension usually corresponds to the thickness of the member, core or article. As used herein, the term "X-Y dimension" refers to the plane orthogonal to the thickness of the member, core or article. The X-Y dimension usually corresponds to the length and width, respectively, of the member, core or article.

As used herein, the term "absorbent core" refers to the component of the absorbent article that is primarily responsible for fluid handling properties of the article, including acquiring, transporting, distributing and storing body fluids. As such, the absorbent core typically does not include the topsheet or backsheet of the absorbent article.

As used herein, the term "absorbent member" refers to the components of the absorbent core that typically provide one or more fluid handling functionality, e.g., fluid acquisition, fluid distribution, fluid transportation, fluid storage, etc. The absorbent member can comprise the entire absorbent core or only a portion of the absorbent core, i.e., the absorbent core can comprise one or more absorbent members. The "storage absorbent member" is the absorbent member component(s) of the absorbent core that function primarily to ultimately store absorbed fluids. As discussed above, the storage absorbent member may also distribute fluid as a result of its vertical wicking capability.

As used herein, the terms "region(s)" or "zone(s)" refer to portions or sections of the absorbent member.

As use herein, the term "layer" refers to an absorbent member whose primary dimension is X-Y, i.e., along its length and width. It should be understood that the term layer is not necessarily limited to single layers or sheets of material. Thus the layer can comprise laminates or combinations of several sheets or webs of the requisite type of materials. Accordingly, the term "layer" includes the terms "layers" and "layered".

For purposes of this invention, it should also be understood that the term "upper" refers to absorbent members, such as layers, that are nearer to the wearer of the absorbent article during use, i.e. towards the topsheet of an absorbent article; conversely, the term "lower" refers to absorbent members that are furthermore away from the wearer of the absorbent article towards the backsheet. Similarly, the term "laterally" corresponds to direction of the shorter dimension of the article, which generally during use corresponds to a left-to-right orientation of the wearer. Longitudinally then refers to the direction perpendicular to the lateral one, but not corresponding to the thickness direction.

All percentages, ratios and proportions used herein are calculated by weight unless otherwise specified.

Absorbent Structures

Absorbent structures according to the present invention comprise at least two elements, namely an ultimate storage absorbent member to essentially ultimately store the liquid received by the structure, and a wrap sheet to support maintaining of the materials comprised in the storage absorbent member therein. Both these elements will now be described with regard to their required properties, suitable embodiments, and their relative arrangement.

Storage Absorbent Members

Suitable storage absorbent members can be of essentially unitary or homogeneous composition, or can be composed of more than one absorbent members or structures, which might consist of sub-structures, such that an absorbent core can be considered to be composed of one or—as in most cases of modern absorbent article designs—several different "materials". Thus, an absorbent member can be tested for its properties either as the total structure, or by assessing the materials or sub-structures comprised therein, independent of whether the material is a "pure" material (e.g. a particle of superabsorbent material), an accumulation of homogeneous material (e.g. a mass of cellulose fibers, or a foam structure, or a mass of superabsorbent particles), a mixture of two or more pure materials or material accumulations (e.g. a mixture of superabsorbent particles having different properties, or a blend of superabsorbent particles and cellulosic fibers); or a further arrangement of several materials forming a distinctable absorbent member (such as a two layer composite).

The present invention is particularly suitable the contain particulate absorbent material, but can also be useful for other forms or shapes, such as fibers or foams.

The storage absorbent members suitable for being used for the present invention have to have a good fluid retention capability, especially under pressure, such as can be assessed in the Performance under pressure test as described hereinafter.

Suitable materials should have a Performance under pressure capacity of at least 23 g/g, preferably more than 25 g/g, still more preferably at least 27 g/g and most preferably more than about 29 g/g.

In addition to this property, the materials should also have a good liquid permeability, such as can be assessed by the Saline Flow Conductivity test as described hereinafter.

Suitable materials should have at least $8*10^{-7}$ cm3 sec/g, preferably $30*10^{-7}$ cm3 sec/g, more preferably more than $50*10^{-7}$ cm3 sec/g, and even more preferably more than $100*10^{-7}$ cm3 sec/g.

Such properties as well as other relevant parameter are described in more detail in EP-A-0 752 982, which is incorporated herein by reference. In particular the PUP and the SFC values allow to select materials, which allow use in relatively high concentrations when forming an absorbent member in combination with other materials, such as with airfelt fibers, synthetic fibers, or other porous materials as foams. A preferred execution of the foamed materials are hydrophilic open celled foams made by the High Internal Phase Emulsion polymerization process, such as well described in U.S. Pat. No. 5,260,345 (DesMarais et al.), U.S. Pat. No. 5,387,207 (Dyer et al.), U.S. Pat. No. 5,560,222 (DesMarais et al.).

Generally, in such structures, the particulate materials will not be completely free to move, but the storage absorbent member will have a certain internal integrity, such as can be achieved by embedding particulate material in a porous structure, such as an air-felt batt of cellulosic fibers, which might thereby present the complementary amount of material. Alternatively, such particles might be bonded to each other, to fibers and the like such as by adhesives, and also a laminated structure of particulate material in combination with the hereinafter described wrap sheets is contemplated. Alternatively, the particles might form a fluid stable aggregate sheet, such as described in PCT publication WO91/15368, or U.S. Pat. No. 5,102,597.

In particular, the concentrations of the superabsorbent materials should be at least 40%, preferably more than 50%, even more preferably more than 60%, and most preferably even more than 70% or 80%, or even more than 90%. Even very high concentrations reaching to essentially pure material being encased by the wrap sheet are contemplated herein, or superabsorbent material macro-structures created by particle-to-particle cross-linking of superabsorbent particles.

In any case, the absorbent member materials which will have to be retained by the wrap sheet can be the material as such (e.g. when particulate material are comprised), or can greater be unintentional, unavoidable or other elements such as break up during the manufacturing, transport, or use of the article.

The shape and form of the storage absorbent member useful for the present invention is not critical, it can have various shapes and forms. Thus, when considering their x-y-directional extension, these can be essentially rectangular, or oval, or hour-glass shape and so on. Also the z-directional extension (thickness) can be uniform or profiled. Generally, the absorbent member will have a x-y-directional extension larger than the thickness dimension, and generally, the absorbent member will have six surfaces, i.e. a top surface oriented towards the wearer during its intended use, a bottom surface opposite said top surface, two laterally extending surfaces (front and back parts of the article during use) two longitudinally extending side surfaces connecting the laterally extending ones.

Wrap Sheets

Non-woven wrap-sheets useful for the present invention are webs, which have the primary functionality of containing materials of the storage absorbent member therein without detrimentally impacting on the fluid handling properties of the storage absorbent member, even for subsequent gushes. Henceforth, the wrap-sheets should be permeable to aqueous liquids, such as by being porous like fibrous webs, or perforated film materials. However, this requirement can be in contradiction with the containment functionality, as storage absorbent member materials may penetrate undesirably through such pores or openings.

The containment functionality can be well described by the pore size and pore size distribution of the web. This functionality can be well achieved by webs by having small mean pore sizes, such as of less than about 30 $\mu m$ when measured by the Coulter Porometer Mean flow Pore size and Pore size distribution test in accordance with ASTM Test method F316-86 as described therein, and such aspects are discussed in U.S. Pat. No. 5,458,592 (Abuto).

Such webs can be made by using fibers having a small fiber diameter, such as conventionally expressed by the "weight in g per 10000 m of fiber length", expressed in dTex.

Useful fibers have a dTex value of less than 1.2 dTex, preferably less than 0.9 dTex, and even more preferably less than 0.7 dTex.

Such webs can be produced by special spun bonding processes, by carding of small diameter fibers such as disclosed in EP-A- 0 619 393, or as a currently preferred option by melt-blowing process. Such processes can produce fiber diameters even lower than 0.2 dTex.

In a preferred embodiment, such pore sizes can be achieved by webs comprising melt-blown webs made from polymers such as poly-propylene. Optionally, such melt-blown webs can form part of a laminate structure, such as when being combined with spun-bonded layer or optionally with other layers, such as carded ones, whereby each of the individual elements are well known in the art.

However, such small pore sized webs of hydrophobic polymers provide a significant barrier for fluid transport, such that the materials useful for the present invention not only have a hydrophilicity which is diminishing after initial wetting such as with conventional materials e.g. Triton X-102, such as suggested in U.S. Pat. No. 5,458,592, but rather have a hydrophilicity which is maintained even after repeated wettings with subsequent removal of the liquid.

When the hydrophilicity properties of non-woven materials are to be assessed, the EDANA strike-through method 150.3-96 has been found wide application and is well known to the man in the art. Whilst this method is generally applied to assess the performance of top-sheet materials rather than wrap-sheet materials, it has been found to also present a the basis for a method to describe wrap sheet materials suitable for the present invention. The testing equipment is essentially unmodified, except for the use of 10 layers of pick-up filter paper supplied by Ahlstrøm, Aahus, Denmark, grade 989. The modifications of the testing procedure are as follows: First, before the test, the contours of the test equipment are marked on the sample specimen, so as to allow re-positioning of the equipment on the exact position of the test specimen. Then, the strike-through test is executed with 5 ml of 0.9% saline solution, according to the test, and the strike-through time (in seconds) is recorded. Then the test plate of the equipment is carefully removed. The sample is also carefully removed and rinsed in a suitable beaker in 400 ml of de-ionized water for 30 seconds. Then, the sample is fixed by two clamps attached to the corners of the web, and dried hanging in an oven at 37° C. for 15 minutes. Subsequently, the strike-through test is executed with the same sample a second type, thereby using a new staple of pick-up paper, and the repeated strike-through time is recorded. The test is repeated at least five times with different sample sheet of one type of web, and average strike-through time as well as deviation is recorded.

Whilst conventionally hydrophilized melt-blown webs as well as materials suitable for the present invention exhibit low strike-through time for the first gush of typically 2 seconds or less, conventional webs loose their hydrophilicity during the washing step of the test (simulating the emptying of pores by well performing fluid storage members), and almost form a barrier to fluid penetration, such as can be seen by an increase in average strike-through times, accompanied by an increase in variability.

This is not surprising, as such webs are known for being useful as barrier materials in absorbent articles, such as for so-called barrier leg-cuff materials.

An example for such a hydrophilized wrap material is commercially available from BBA COROVIN GmbH, Peine, Germany, under the trade designation MD 2000 H, as a laminate made of two layers of PP fibers, namely 12 gsm basis weight of spun-bonded web, and 2 gsm basis weight of melt-blown web, with application of a conventional surfactant. For this web, the average strike-through penetration increases dramatically from about 1.5 seconds for the first test to more than 60 seconds in the second test, as described in the above. As will be shown hereinafter, such webs are not suitable for specific preferred core designs.

However, surprisingly, it has been found, that melt-blown web materials can provide useful wrap-sheet materials, provided the materials maintain their hydrophilicity even after being wetted and re-dried, thus having an average second strike-through time of less than 60 seconds, preferably less than 30 seconds, more preferably less than 10 seconds, even more preferably less than 5 seconds.

A particularly preferred execution of such materials is an analogue to the above material, all being the same, except for utilizing a more permanent hydrophilic finish or surfactant. Such a material can be received from the same company as above, BBA COROVIN, Peine, Germany, under the designation MB 2000 HPC2, and exhibits a similar strike-through time in the first gush of about 1.5 seconds, but has only an increase in strike-through time to not more than about 2.5 seconds for the second gush.

Improved Absorbent Structures

Having thus described the two essential elements for the present invention, the improved absorbent structures according to the present invention comprise at least one of these above describe absorbent structures, and at least one of these above described wrap sheets.

The wrap sheet has to cover the absorbent structure at least at a part of the surface of the absorbent structure, such that the fluid path from the liquid receiving area to the absorbent structure will pass through the web. Thus the meaning of the term "wrapping" should not be read to mean complete wrapping or enveloping only. An example for such an embodiment can be a wrap-sheet covering the top surface of the absorbent structure, and then being tacked down next to the core, such that the side surface can be but not necessarily have to be covered by the wrap sheet.

In a preferred embodiment, the wrap-sheet covers also other surfaces of the absorbent member, in one preferred embodiment, it covers all six surfaces, such that the absorbent member is completely enveloped. Another preferred and more easy to manufacture embodiment covers the top surface as well as two side surfaces by being folded around these to partly of fully cover the bottom surface.

The wrapping of the absorbent member can also be achieved by more than more than one wrap-sheet, or by one wrap sheet with different properties in different regions thereof. For example, the surface parts of the absorbent member which are not in the fluid flow path, can have no, or non-permanent fluid hydrophilicity. Or, a different wrap material can be used in such regions, or the absorbent member materials can there be contained by other elements, such as conventional tissue materials, but also impermeable sheets, which may at the same time has other functionality, such as a backsheet material.

Of course, it is an essential requirement, that the absorbent structure and the wrap sheet are in fluid communication with each other, such that the fluid flow path, and particularly the capillary transport gradient will not be interrupted. A preferred embodiment of this is a design, where the wrap sheet and the absorbent structure are in direct contact with each other—at least for the surfaces as described in the above.

In order to further demonstrate the benefits of the present invention, absorbent structure have been made by essentially homogeneously mixing various superabsorbent polymer types with cellulosic air-felt, and then combining these with various wrap sheets.

In order to show the improved performance, the above mentioned test has been modified further, essentially by replacing the pick-up paper by the absorbent structures. Then, the absorbent structure is tested without any wrapping, and then with the respective wrapping. As for the strike-through test, the test fluid is 5 ml of 0.9% saline solution. Here, the test is repeated three time with 1 minute waiting time between each gush.

Whilst the absolute strike through times are highly dependent of the absorbent structure, it has been found that selecting the parameter for the test provides a meaningful tool for distinguishing the various webs within a meaningful context for an absorbent structure. It has been found, that with well performing absorbent structures suitable combinations with wrap sheets show no or only a small increase in strike-through times, whereas unsuitable webs show a marked increase.

The results of the test with various structures as described below are summarized in Table 1.

TABLE 1

| Abs. Struct | Core Wrap | Absorbent structure/core wrap strike-through (seconds) | | |
|---|---|---|---|---|
| | | $1^{st}$ | $2^{nd}$ | $3^{rd}$ |
| C1 | A0 | 1.2 | 6.4 | 13.5 |
| C1 | A1 | 1.2 | 7.8 | 40.6 |
| C1 | A2 | 1.6 | 6.8 | 12.6 |
| C2 | A0 | 1.5 | 4.5 | 8.8 |
| C2 | A1 | 1.9 | 11.2 | 30.8 |
| C2 | A2 | 1.6 | 5.7 | 11.0 |
| C3 | A1 | 1.4 | 3.1 | 5.1 |
| C3 | A2 | 1.3 | 2.4 | 3.8 |

First, a core structure sample C1 was prepared by essentially homogeneously mixing Northern Softwood Kraft pulp and superabsorbent material as commercially available from Stockhausen GmbH, Krefeld, Germany, under the code SXM 6860. The total basis weight of the materials was about 700 gsm, the concentration of the superabsorbent material about 67%, and the overall density at 31.8 g/cm2 was about 0.253 g/cm3. The superabsorbent material exhibits a PUP value of about 32.5 g/g and an SFC value of about 4×10–7 cm3 sec/g.

This absorbent structure was tested with no wrap-sheet (A0), with the non-permanently hydrophilized (comparative) wrap sheet as described in the above (A1), and with the permanently hydrophilic wrap-sheet as described in the above (A2).

The results in Table 1 clearly demonstrate the improvements of the A2-type wrap-sheet.

Second, a Core structure sample C2 was prepared by essentially homogeneously mixing Northern Softwood Kraft pulp and superabsorbent material as commercially available from Stockhausen GmbH, Krefeld, Germany, under the code SXM 65170. The total basis weight of the materials was about 700 gsm, the concentration of the superabsorbent material about 67%, and the overall density at 31.8 g/cm2 was about 0.253 g/cm3. The superabsorbent material exhibits a PUP value of about 32.5 g/g and an SFC value of about 80×10−7 cm3 sec/g.

This absorbent structure was tested with no wrap-sheet (A0), with the non-permanently hydrophilized (comparative) wrap sheet as described in the above (A1), and with the permanently hydrophilic wrap-sheet as described in the above (A2).

Also, the benefits of this combination are clear from Table 1.

Thirdly, as a comparative example for an absorbent stucture, sample C3 was prepared by essentially homogeneously mixing Northern Softwood Kraft pulp and superabsorbent material as commercially available from Stockhausen GmbH, Krefeld, Germany, under the code SXM 100. The total basis weight of the materials was about 773 gsm, the concentration of the superabsorbent material about 22%, and the density at 31.8 g/cm2 was about 0.105 g/cm3. The superabssorbent material exhibits a PUP value of about 26 g/g and an SFC value of about less than 1×10−7 cm3 sec/g.

This absorbent structure was tested with the non-permanently hydrophilized (comparative) wrap sheet as described in the above (A1), and with the permanently hydrophilic wrap-sheet as described in the above (A2). Herein, the differences between the two types of wrap-sheets become much smaller.

Absorbent Articles

The absorbent structures of the present invention are particularly useful to be used in absorbent articles.

An absorbent article generally comprises:

an absorbent core, which comprises the absorbent member according to the present invention, and—optionally but often preferably—other fluid handling members such as fluid acquisition and/or distribution member.;

a fluid pervious topsheet;

a fluid impervious backsheet;

optionally further features like closure elements or elastification.

FIG. 1 is a plan view of an exemplary embodiment of an absorbent article which can comprise the absorbent structure according to the present, invention which is a diaper.

The diaper 20 is shown in FIG. 1 in its flat-out, uncontracted state (i.e. with elastic induced contraction pulled out except in the side panels wherein the elastic is left in its relaxed condition) with portions of the structure being cut-away to more clearly show the construction of the diaper 20 and with the portion of the diaper 20 which faces away from the wearer, the outer surface 52, facing the viewer. As shown in FIG. 1, the diaper 20 comprises a liquid pervious topsheet 24, a liquid impervious backsheet 26 joined with the topsheet 24, and an absorbent core 28 positioned between the topsheet 24 and the backsheet 26; elasticized side panels 30; elasticized leg cuffs 32; an elastic waist feature 34; and a closure system comprising a dual tension fastening system generally multiply designated as 36. The dual tension fastening system 36 preferably comprises a primary fastening system 38 and a waist closure system 40. The primary fastening system 38 preferably comprises a pair of securement members 42 and a landing member 44. The waist closure system 40 is shown in FIG. 1 to preferably comprise a pair of first attachment components 46 and a second attachment component 48. The diaper 20 also preferably comprises a positioning patch 50 located subjacent each first attachment component 46.

The diaper 20 is shown in FIG. 1 to have an outer surface 52 (facing the viewer in FIG. 1), an inner surface 54 opposed to the outer surface 52, a first waist region 56, a second waist region 58 opposed to the first waist region 56, and a periphery 60 which is defined by the outer edges of the diaper 20 in which the longitudinal edges are designated 62 and the end edges are designated 64. The inner surface 54 of the diaper 20 comprises that portion of the diaper 20 which is positioned adjacent to the wearer's body during use (i.e. the inner surface 54 generally is formed by at least a portion of the topsheet 24 and other components joined to the topsheet 24). The outer surface 52 comprises that portion of the diaper 20 which is positioned away from the wearer's body (i.e. the outer surface 52 generally is formed by at least a portion of the backsheet 26 and other components joined to the backsheet 26). The first waist region 56 and the second waist region 58 extend, respectively, from the end edges 64 of the periphery 60 to the lateral centerline 66 of the diaper 20. The waist regions each comprise a central region 68 and a pair of side panels which typically comprise the outer lateral portions of the waist regions. The side panels positioned in the first waist region 56 are designated 70 while the side panels in the second waist region 58 are designated 72. While it is not necessary that the pairs of side panels or each side panel be identical, they are preferably mirror images one of the other. The side panels 72 positioned in the second waist region 58 can be elastically extensible in the lateral direction (i.e. elasticized side panels 30). (The lateral direction (x direction or width) is defined as the direction parallel to the lateral centerline 66 of the diaper 20; the longitudinal direction (y direction or length) being defined as the direction parallel to the longitudinal centerline 67; and the axial direction (Z direction or thickness) being defined as the direction extending through the thickness of the diaper 20).

FIG. 1 shows a specific execution of the diaper 20 in which the topsheet 24 and the backsheet 26 are unitary across the core and the chassis region and have length and width dimensions generally larger than those of the absorbent core 28. The topsheet 24 and the backsheet 26 extend beyond the edges of the absorbent core 28 to thereby form the periphery 60 of the diaper 20. The periphery 60 defines the outer perimeter or, in other words, the edges of the diaper 20. The periphery 60 comprises the longitudinal edges 62 and the end edges 64.

While each elasticized leg cuff 32 may be configured so as to be similar to any of the leg bands, side flaps, barrier cuffs, or elastic cuffs described above, it is preferred that each elasticized leg cuff 32 comprise at least an inner barrier cuff 84 comprising a barrier flap 85 and a spacing elastic member 86 such as described in the above-referenced U.S. Pat. No. 4,909,803. In a preferred embodiment, the elasticized leg cuff 32 additionally comprises an elastic gasketing cuff 104 with one or more elastic strands 105, positioned outboard of the barrier cuff 84 such as described in the above-references U.S. Pat. No. 4,695,278.

The diaper 20 may further comprise an elastic waist feature 34 that provides improved fit and containment. The elastic waist feature 34 at least extends longitudinally outwardly from at least one of the waist edges 83 of the absorbent core 28 in at least the central region 68 and generally forms at least a portion of the end edge 64 of the diaper 20. Thus, the elastic waist feature 34 comprises that portion of the diaper at least extending from the waist edge 83 of the absorbent core 28 to the end edge 64 of the diaper 20 and is intended to be placed adjacent the wearer's waist.

Disposable diapers are generally constructed so as to have two elastic waist features, one positioned in the first waist region and one positioned in the second waist region.

The elasticized waist band 35 of the elastic waist feature 34 may comprise a portion of the topsheet 24, a portion of the backsheet 26 that has preferably been mechanically stretched and a bi-laminate material comprising an elastomeric member 76 positioned between the topsheet 24 and backsheet 26 and resilient member 77 positioned between backsheet 26 and elastomeric member 76.

This as well as other components of the diaper are given in more detail in WO 93/16669 which is incorporated herein by reference.

The absorbent core 28 comprises at least one absorbent structure, and at least one non-woven core wrap web of the melt-blown type. Optional components as acquisition and/or distribution members are not shown in the figure, nor optimal arrangements with e.g. two absorbent structures.

In addition to the above described core structure and the respective wrap sheet, the absorbent article can preferably comprise additional fluid handling members, such a so called acquisition member in form of synthetic fibrous webs, and/or structures comprising stiffened cellulose webs, preferably cross-linked cellulose fibers, and/fluid distribution members, and or further fluid storage members, which do not require wrapping, uch a open porous foam structures in a sheet or layered form.

While it is preferred to have a topsheet as the material nearest the wearer's skin, it is not necessary. It is contemplated that a suitable absorbent core configuration could be used without a topsheet and still produce desirable results such as comfort and absorbency as well as simplicity in manufacturing and material cost savings. For example, the body-side surface of the absorbent core itself could be made of liquid pervious, soft, compliant, non-irritating materials that substitute for a separate topsheet. Such an absorbent core would only need to be used in combination with a backsheet to provide for comfort and absorbency in an absorbent article.

Test Methods

1. Saline Flow Conductivity (SFC)

This test determines the Saline Flow Conductivity (SFC) of the gel layer formed from superabsorbent material or—as referred to hereinafter—hydrogel-forming absorbent polymer that is swollen in Jayco synthetic urine under a confining pressure. The objective of this test is to assess the ability of the hydrogel layer formed from a hydrogel-forming absorbent polymer to acquire and distribute body fluids when the polymer is present at high concentrations in an absorbent member and exposed to usage mechanical pressures. Darcy's law and steady-state flow methods are used for determining saline flow conductivity. (See, for example, "Absorbency," ed. by P. K. Chatterjee, Elsevier, 1985, Pages 42–43 and "Chemical Engineering Vol. 11, Third Edition, J. M. Coulson and J. F. Richardson, Pergamon Press, 1978, Pages 125–127.)

The hydrogel layer used for SFC measurements is formed by swelling a hydrogel-forming absorbent polymer in Jayco synthetic urine for a time period of 60 minutes. The hydrogel layer is formed and its flow conductivity measured under a mechanical confining pressure of 0.3 psi (about 2 kPa). Flow conductivity is measured using a 0.118 M NaCl solution. For a hydrogel-forming absorbent polymer whose uptake of Jayco synthetic urine versus time has substantially leveled off, this concentration of NaCl has been found to maintain the thickness of the hydrogel layer substantially constant during the measurement. For some hydrogel-forming absorbent polymers, small changes in hydrogel-layer thickness can occur as a result of polymer swelling, polymer deswelling, and/or changes in hydrogel-layer porosity. A constant hydrostatic pressure of 4920 dyne/cm2 (5 cm of 0.118M NaCl) is used for the measurement.

Flow rate is determined by measuring the quantity of solution flowing through the hydrogel layer as a function of time. Flow rate can vary over the duration of the measurement. Reasons for flow-rate variation include changes in the thickness of the hydrogel layer and changes in the viscosity of interstitial fluid, as the fluid initially present in interstitial voids (which, for example, can contain dissolved extractable polymer) is replaced with NaCl solution. If flow rate is time dependent, then the initial flow rate, typically obtained by extrapolating the measured flow rates to zero time, is used to calculate flow conductivity. The saline flow conductivity is calculated from the initial flow rate, dimensions of the hydrogel layer, and hydrostatic pressure. For systems where the flow rate is substantially constant, a hydrogel-layer permeability coefficient can be calculated from the saline flow conductivity and the viscosity of the NaCl solution.

Figure 2A:
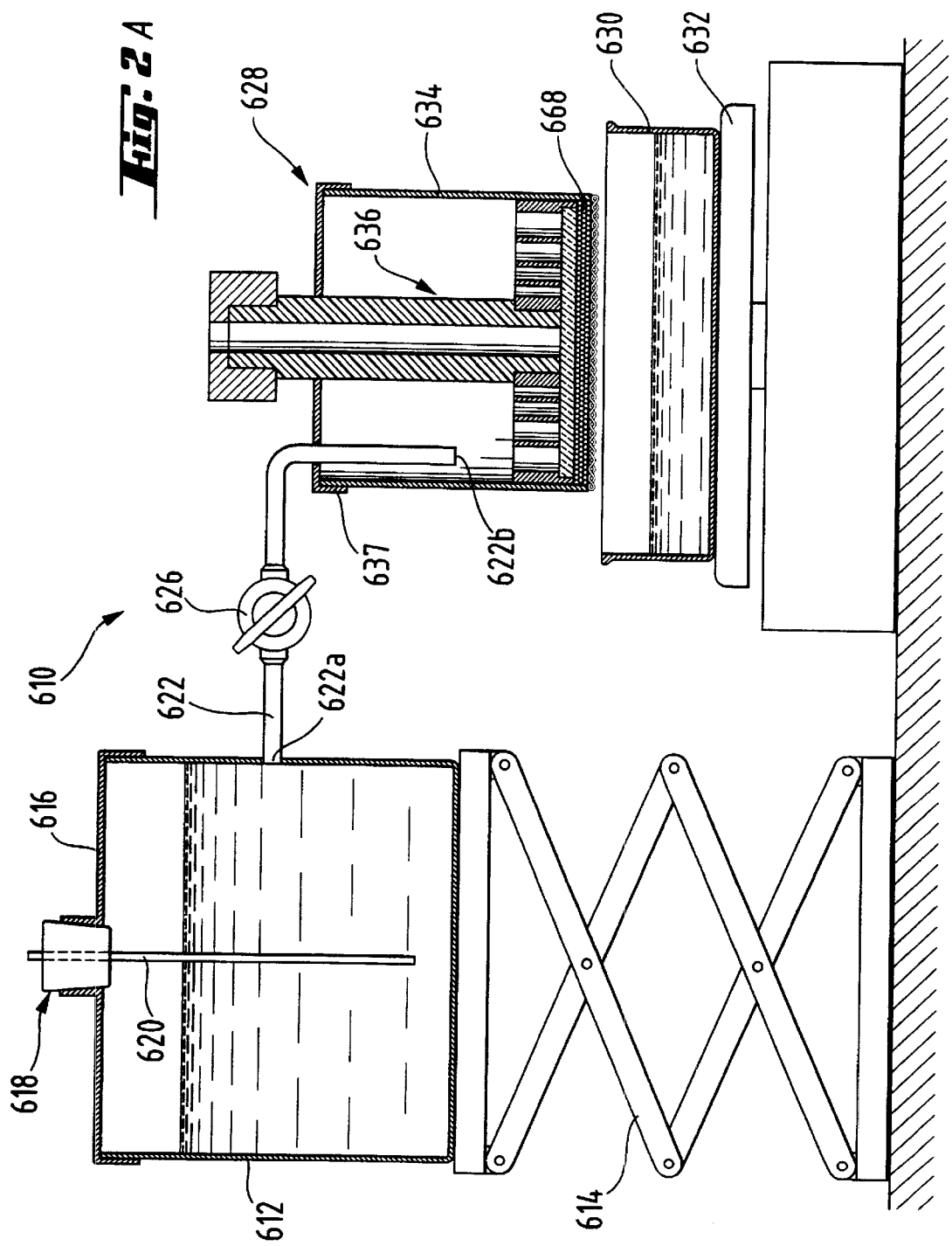

A suitable apparatus 610 for this test is shown in FIG. 2A. This apparatus includes a constant hydrostatic head reservoir indicated generally as 612 that sits on a laboratory jack indicated generally as 614. Reservoir 612 has lid 616 with a stoppered vent indicated by 618 so that additional fluid can be added to reservoir 612. An open-ended tube 620 is inserted through lid 616 to allow air to enter reservoir 612 for the purpose of delivering fluid at a constant hydrostatic pressure. The bottom end of tube 620 is positioned so as to maintain fluid in cylinder 634 at a height of 5.0 cm above the bottom of hydrogel layer 668 (see FIG. 2B).

Reservoir 612 is provided with a generally L-shaped delivery tube 622 having an inlet 622a that is below the surface of the fluid in the reservoir. The delivery of fluid by tube 622 is controlled by stopcock 626. Tube 622 delivers fluid from reservoir 612 to a piston/cylinder assembly generally indicated as 628. Beneath assembly 628 is a support screen (not shown) and a collection reservoir 630 that sits on a laboratory balance 632.

Figure 2B:
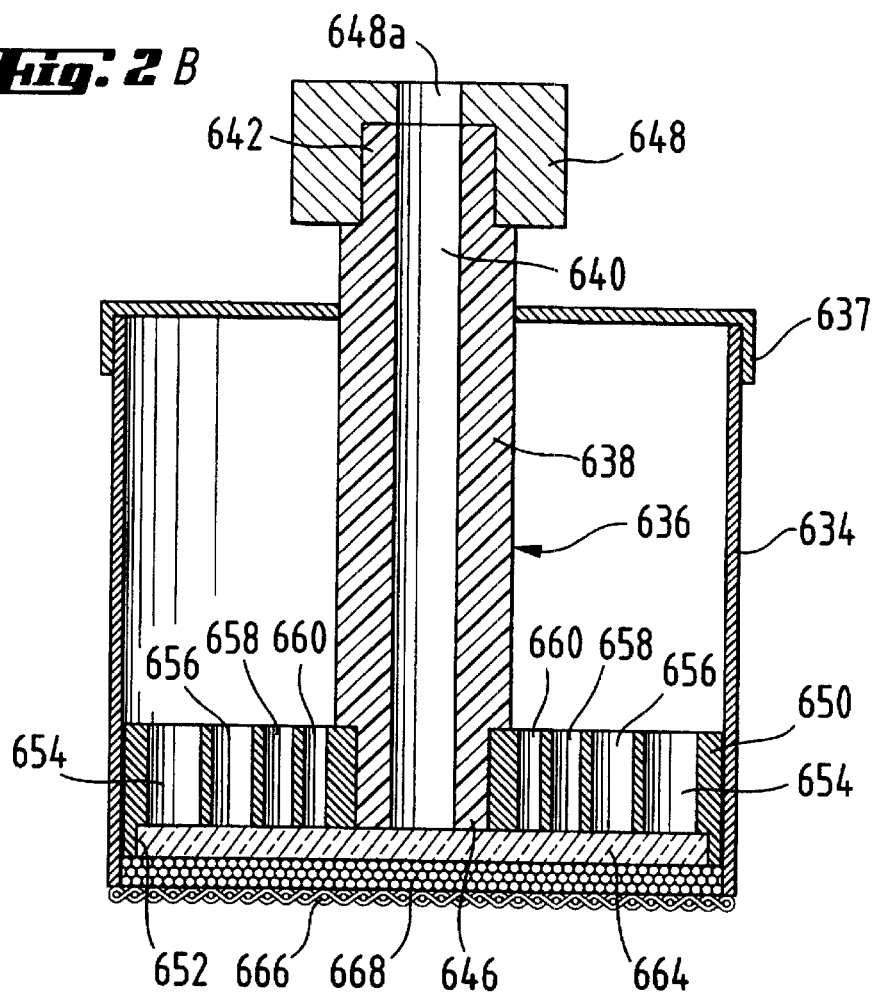

Referring to FIG. 2A, assembly 628 basically consists of a cylinder 634, a piston generally indicated as 636 and a cover 637 provided with holes for piston 636 and delivery tube 622. As shown in FIG. 2A, the outlet 622b of tube 622 is positioned below the bottom end of tube 620 and thus will also be below the surface of the fluid (not shown) in cylinder 634. As shown in FIG. 2B, piston 636 consists of a generally cylindrical LEXAN" shaft 638 having a concentric cylindrical hole 640 bored down the longitudinal axis of the shaft. Both ends of shaft 638 are machined to provide ends 642 and 646. A weight indicated as 648 rests on end 642 and has a cylindrical hole 648a bored through the center thereof.

Figure 2C:
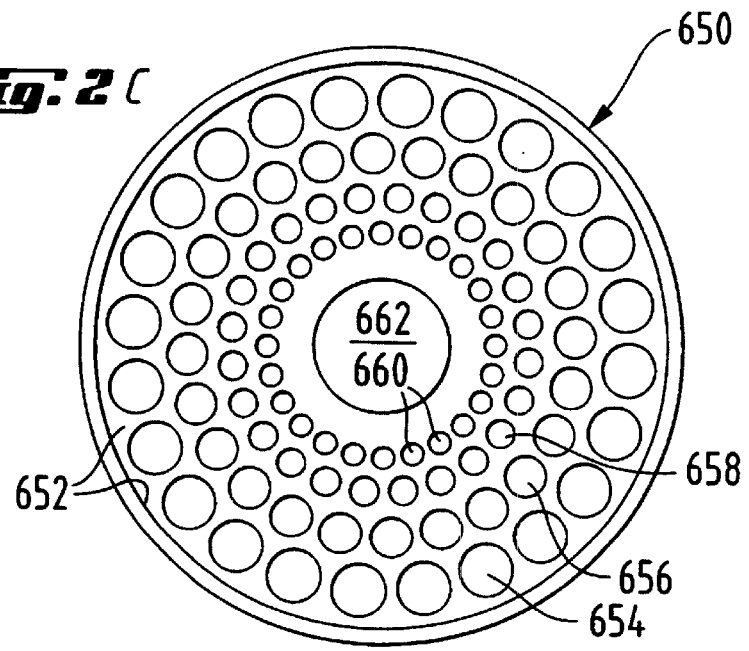

Inserted on the other end 646 is a generally circular Teflon piston head 650 having an annular recess 652 in the bottom thereof. Piston head 650 is sized so as to slidably move inside cylinder 634. As particularly shown in FIG. 2C, piston head 650 is provided with four concentric rings of twenty-four cylindrical holes each indicated generally as 654, 656, 658, and 660. As can be seen in FIG. 2C, concentric rings 654 to 660 fit within the area defined by recess 652. The holes in each of these concentric rings are bored from the top to bottom of piston head 650. The holes in each ring are spaced by approximately 15 degrees and offset by approximately 7.5 degrees from the holes in adjacent rings. The holes in each ring have a progressively smaller diameter going inwardly from ring 654 (0.204 inch diameter) to ring 660 (0.111 inch diameter). Piston head 650 also has cylindrical hole 662 bored in the center thereof to receive end 646 of shaft 638.

As shown in FIG. 2B, a fritted circular glass disc 664 fits within recess 652. Attached to bottom end of cylinder 634 is a No. 400 mesh stainless steel cloth screen 666 that is biaxially stretched to tautness prior to attachment. The sample of hydrogel-forming absorbent polymer indicated as 668 is supported on screen 666.

Cylinder 634 is bored from a transparent LEXAN" rod or equivalent and has an inner diameter of 6.00 cm (area=28.27 cm2), a wall thickness of approximately 0.5 cm, and a height of approximately 6.0 cm. Piston head 650 is machined from a solid Teflon rod. It has a height of 0.625 inches and a diameter that is slightly less than the inner diameter of cylinder 634, so that it fits within the cylinder with minimum wall clearances, but still slides freely. Recess 652 is approximately 56 mm in diameter by 4 mm deep. Hole 662 in the center of the piston head 650 has a threaded 0.625 inch opening (18 threads/inch) for end 646 of shaft 638. Fritted disc 664 is chosen for high permeability (e.g., Chemglass Cat No. CG-201-40, 60 mm diameter; X-Coarse Porosity) and is ground so that it fits snugly within recess 652 of piston head 650, with the bottom of the disc being flush with the bottom of the piston head. Shaft 638 is machined from a LEXAN" rod and has an outer diameter of 0.875 inches and an inner diameter of 0.250 inches. End 646 is approximately 0.5 inches long and is threaded to match hole 662 in piston head 650. End 642 is approximately an inch long and 0.623 inches in diameter, forming an annular shoulder to support the stainless steel weight 648. Fluid passing through the hole 640 in shaft 638 can directly access the fritted disc 664. The annular stainless steel weight 648 has an inner diameter of 0.625 inches, so that it slips onto end 642 of shaft 638 and rests on the annular shoulder formed therein. The combined weight of fritted glass disc 664, piston 636 and weight 648 equals 596 g, which corresponds to a pressure of 0.3 psi for an area of 28.27 cm2. Cover 637 is machined from LEXAN" or its equivalent and is dimensioned to cover the top of cylinder 634. It has an 0.877 inch opening in the center thereof for shaft 638 of piston 636 and a second opening near the edge thereof for delivery tube 622.

The cylinder 634 rests on a 16 mesh rigid stainless steel support screen (not shown) or equivalent. This support screen is sufficiently permeable so as to not impede fluid flow into the collection reservoir 630. The support screen is generally used to support cylinder 634 when the flow rate of saline solution through assembly 628 is greater than about 0.02 g/sec. For flow rates less than about 0.02 g/sec, it is preferable that there be a continuous fluid path between cylinder 634 and the collection reservoir. This can be accomplished by positioning cylinder 634 on a fritted disc in fritted funnel which is connected to tubing leading into the liquid reservoir 630.

Jayco synthetic urine used in this method is prepared by dissolving a mixture of 2.0 g KCL, 2.0 g Na2SO4, 0.85 g NH4H2PO4, 0.15 g (NH4)2HPO4, 0.19 g CaCl2, and 0.23 g MgCl2 to 1.0 liters with distilled water. The salt mixture can be purchased from Endovations, Reading, Pa. (cat No. JA-00131-000-01).

The 0.118 M NaCl solution is prepared by dissolving 6.896 g NaCl (Baker Analyzed Reagent or equivalent) to 1.0 liters with distilled water.

An analytical balance 632 accurate to 0.01 g (e.g., Mettler PM4000 or equivalent) is typically used to measure the quantity of fluid flowing through the hydrogel layer 668 when the flow rate is about 0.02 g/sec or greater. A more accurate balance (e.g., Mettler AE200 or equivalent) can be needed for less permeable hydrogel layers having lower flow rates. The balance is preferably interfaced to a computer for monitoring fluid quantity versus time.

The thickness of hydrogel layer 668 in cylinder 634 is measured to an accuracy of about 0.1 mm. Any method having the requisite accuracy can be used, as long as the weights are not removed and the hydrogel layer is not additionally compressed or disturbed during the measurement. Using a caliper gauge (e.g., Manostat 15-100-500 or equivalent) to measure the vertical distance between the bottom of the stainless steel weight 648 and the top of cover 637, relative to this distance with no hydrogel layer 668 in cylinder 634 is acceptable. Also acceptable is the use of a depth gauge (e.g., Ono Sokki EG-225 or equivalent) to measure the position of piston 636 or stainless steel weight 648 relative to any fixed surface, compared to its position with no hydrogel layer in cylinder 634.

The SFC measurement is performed at ambient temperature (i.e., 20° C.–25° C.) and is carried out as follows:

0.9 gm aliquot of hydrogel-forming absorbent polymer (corresponding to a basis weight of 0.032 gm/cm2) is added to cylinder 634 and distributed evenly on screen 666. For most hydrogel-forming absorbent polymers, moisture content is typically less than 5%. For these, the quantity of hydrogel-forming absorbent polymer to be added can be determined on a wet-weight (as is) basis. For hydrogel-forming absorbent polymers having a moisture content greater than about 5%, the added polymer weight should be corrected for moisture (i.e., the added polymer should be 0.9 g on a dry-weight basis). Care is taken to prevent hydrogel-forming absorbent polymer from adhering to the cylinder walls. Piston 636 (minus weight 648) with disc 664 positioned in recess 652 of piston head 650 is inserted into cylinder 634 and positioned on top of the dry hydrogel-forming absorbent polymer 668. If necessary, piston 636 can be turned gently to more-uniformly distribute the hydrogel-forming absorbent polymer on screen 666. Cylinder 634 is the covered with cover 637 and weight 648 is then positioned on end 642 of shaft 638.

A fritted disc (coarse or extra coarse) having a diameter greater than that of cylinder 634 is positioned in a wide/shallow flat-bottomed container that is filled to the top of the fritted disc with Jayco synthetic urine. The piston/cylinder assembly 628 is then positioned on top of this fritted glass disc. Fluid from the container passes through the fritted disc and is absorbed by the hydrogel-forming absorbent polymer 668. As the polymer absorbs fluid, a hydrogel layer is formed in cylinder 634. After a time period of 60 minutes, the thickness of the hydrogel layer is determined. Care is taken that the hydrogel layer does not lose fluid or take in air during this procedure.

The piston/cylinder assembly 628 is then transferred to apparatus 610. The support screen (not shown) and any gap between it and the piston/cylinder assembly 628 is presaturated with saline solution. If the fritted funnel 718 of the PUP apparatus 710 is used to support cylinder 634, the surface of the fritted funnel should be minimally elevated relative to the height of the fluid in the collection reservoir, with valves between the fritted funnel and the collection reservoir being in the open position. (The fritted funnel elevation should be sufficient such that fluid passing through the hydrogel layer does not accumulate in the funnel.)

The SFC measurement is initiated by adding NaCl solution through hole 640 in shaft 638 in order to expel air from piston head 650 and then turning stopcock 626 to an open position so that delivery tube 622 delivers fluid to cylinder 634 to a height of 5.0 cm above the bottom of hydrogel layer 668. Although the measurement is considered to have been initiated (to) at the time NaCl solution is first added, the time at which a stable hydrostatic pressure, corresponding to 5.0 cm of saline solution, and a stable flow rate is attained (ts) is noted. (The time ts should typically be about one minute or less.) The quantity of fluid passing through hydrogel layer 668 versus time is determined gravimetrically for a time period of 10 minutes. After the elapsed time, piston/cylinder assembly 628 is removed and the thickness of hydrogel layer 668 is measured. Generally the change in thickness of the hydrogel layer is less than about 10%.

In general, flow rate need not be constant. The time-dependent flow rate through the system, Fs(t) is determined, in units of g/sec, by dividing the incremental weight of fluid passing through the system (in grams) by incremental time (in seconds). Only data collected for times between ts and 10 minutes is used for flow rate calculations. Flow rate results between ts and 10 minutes is used to calculate a value for Fs(t=0), the initial flow rate through the hydrogel layer. Fs(t=0) is calculated by extrapolating the results of a least-squares fit of Fs(t) versus time to t=0.

For a layer having a very high permeability (e.g., a flow rate greater than ~2 g/sec), it may not be practical to collect fluid for the full 10 minute time period. For flow rates greater than ~2 g/sec, the time of collection can be shortened in proportion to the flow rate.

For some hydrogel-forming absorbent polymers having extremely low permeability, absorption of fluid by the hydrogel competes with transport of fluid through the hydrogel layer and either there is no flow of fluid through the hydrogel layer and into the reservoir or, possibly, there is a net absorption of fluid out of the PUP reservoir. For these extremely low permeability hydrogel layers, it is optional to extend the time for Jayco SynUrine absorption to longer periods (e.g., 16 hours).

In a separate measurement, the flow rate through apparatus 610 and the piston/cylinder assembly 628 (Fa) is measured as described above, except that no hydrogel layer is present. If Fa is much greater than the flow rate through the system when the hydrogel layer is present, Fs, then no correction for the flow resistance of the SFC apparatus and the piston/cylinder assembly is necessary. In this limit, Fg=Fs, where Fg is the contribution of the hydrogel layer to the flow rate of the system. However if this requirement is not satisfied, then the following correction is used to calculate the value of Fg from the values of Fs and Fa:

$$Fg=(Fa*Fs)/(Fa-Fs)$$

The Saline Flow Conductivity (K) of the hydrogel layer is calculated using the following equation:

$$K=\{Fg(t=0)*L0\}/\{\rho*A*\Delta P\},$$

where Fg(t=0) is the flow rate in g/sec determined from regression analysis of the flow rate results and any correction due to assembly/apparatus flow resistance, L0 is the initial thickness of the hydrogel layer in cm, $\rho$ is the density of the NaCl solution in gm/cm3. A is the area of the hydrogel layer in cm2, $\Delta P$ is the hydrostatic pressure in dyne/cm2, and the saline flow conductivity, K, is in units of cm3 sec/gm.

The average of three determinations should be reported.

For hydrogel layers where the flow rate is substantially constant, a permeability coefficient ($\kappa$) can be calculated from the saline flow conductivity using the following equation:

$$\kappa=K*\eta$$

where $\eta$ is the viscosity of the NaCl solution in poise and the permeability coefficient, $\kappa$, is in units of cm2.

The following is an example of how SFC is calculated according to the present invention:

The measured value of Fa is 412 g/min=6.87 g/sec. For a single determination on the particulate hydrogel-forming polymer sample 3–5 (Example 3), the extrapolated value for Fs(t=0) is 33.9 g/min=0.565 g/sec, with a very-low ratio of slope:intercept of 9*10−5 sec−1. Correcting for apparatus resistance:

$$Fg=(6.87*0.565)(6.87-0.565)=0.616 \text{ g/sec}$$

Given a 0.118 M saline density of 1.003 g/cm3 (CRC Handbook of Chemistry and Physics, 61st Edition) a hydrogel-layer thickness of 1.134 cm, a hydrogel layer area of 28.27 cm2, and a hydrostatic pressure of 4920 dyne/cm2.

$$K=(0.616*1.134)/(1.003*28.27*4920)=5.0*10-6 \text{ cm3 sec/gm}$$

Considering the substantially constant flow rate and given a 0.118 M saline viscosity of 0.01015 poise (CRC Handbook of Chemistry and Physics, 61st Edition):

$$\kappa=K*\eta=(5.0*10-6)*0.01015=5.1*10-8 \text{ cm2}$$

2. Performance Under Pressure (PUP) Capacity

This test determines the 60 minute gram/gram absorption of synthetic urine for a hydrogel-forming absorbent polymer that is laterally confined in a piston/cylinder assembly under a confining pressure of 0.7 psi (about 5 kPa). The objective of the test is to assess the ability of a hydrogel-forming absorbent polymer layer to absorb body fluids, over a practical period of time, when the polymer is present at high basis weight and high concentrations in an absorbent member and exposed to usage pressures. Usage pressures against which a hydrogel-forming polymer is forced to absorb urine against include mechanical pressures resulting from the weight and/or motions of the wearer, mechanical pressures resulting from elastics and fastening systems, and the hydrostatic suction resulting from adjacent capillary (e.g., fibrous) layers and/or structures as they are drained of fluid.

The test fluid for the PUP capacity test is Jayco synthetic urine. This fluid is absorbed by the hydrogel-forming absorbent polymer under demand absorption conditions at near-zero hydrostatic pressure.

Figure 3A:
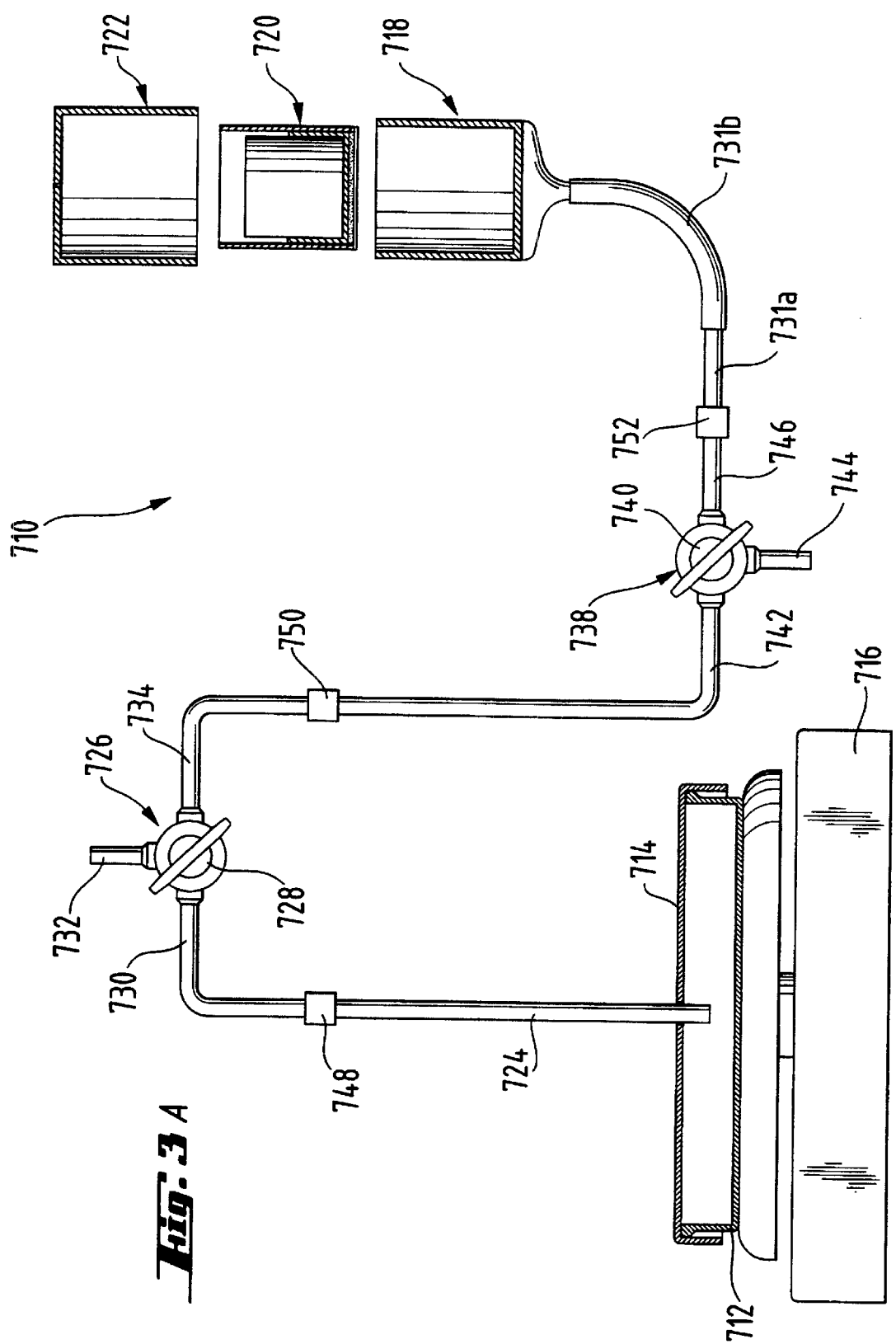

A suitable apparatus 710 for this test is shown in FIG. 3A. At one end of this apparatus is a fluid reservoir 712 (such as a petri dish) having a cover 714. Reservoir 712 rests on an analytical balance indicated generally as 716. The other end of apparatus 710 is a fritted funnel indicated generally as 718, a piston/cylinder assembly indicated generally as 720 that fits inside funnel 718, and cylindrical plastic fritted funnel cover indicated generally as 722 that fits over funnel 718 and is open at the bottom and closed at the top, the top having a pinhole. Apparatus 710 has a system for conveying fluid in either direction that consists of sections glass capillary tubing indicated as 724 and 731a, flexible plastic tubing (e.g., ¼ inch i.d. and ⅜ inch o.d. Tygon tubing) indicated as 731b, stopcock assemblies 726 and 738 and Teflon connectors 748, 750 and 752 to connect glass tubing 724 and 731a and stopcock assemblies 726 and 738. Stopcock assembly 726 consists of a 3-way valve 728, glass capillary tubing 730 and 734 in the main fluid system, and a section of glass capillary tubing 732 for replenishing reservoir 712 and forward flushing the fritted disc in fritted funnel 718. Stopcock assembly 738 similarly consists of a 3-way valve 740, glass capillary tubing 742 and 746 in the main fluid line, and a section of glass capillary tubing 744 that acts as a drain for the system.

Figure 3B:
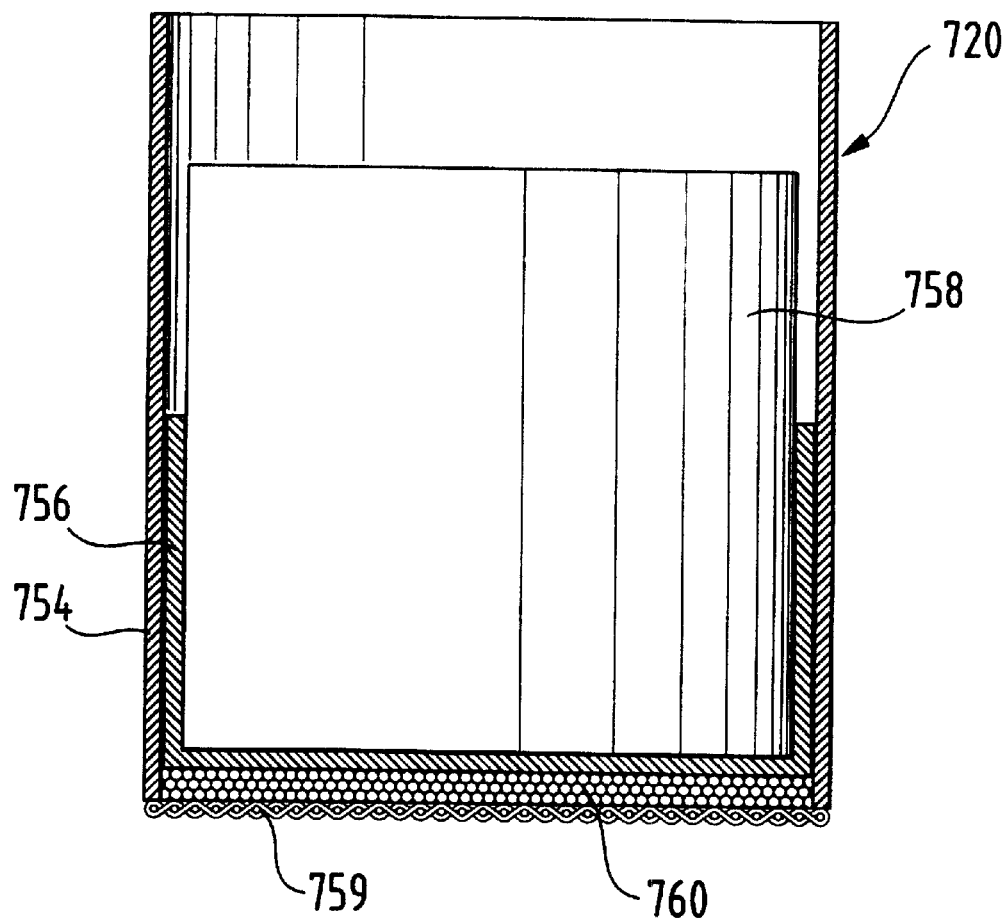

Referring to FIG. 3B, assembly 720 consists of a cylinder 754, a cup-like piston indicated by 756 and a weight 758 that fits inside piston 756. Attached to bottom end of cylinder 754 is a No. 400 mesh stainless steel cloth screen 759 that is biaxially stretched to tautness prior to attachment. Hydrogel-forming absorbent polymer indicated generally as 760 rests on screen 759. Cylinder 754 is bored from a transparent LEXAN" rod (or equivalent) and has an inner diameter of 6.00 cm (area=28.27 cm2), with a wall thickness of approximately 5 mm and a height of approximately 5 cm. The piston 756 is in the form of a Teflon cup and is machined to fit into cylinder 754 within tight tolerances. Cylindrical stainless steel weight 758 is machined to fit snugly within piston 756 and is fitted with a handle on the top (not shown) for ease in removing. The combined weight of piston 756 and weight 758 is 1390 g, which corresponds to a pressure of 0.7 psi for an area of 28.27 cm2.

The components of apparatus 710 are sized such that the flow rate of synthetic urine therethrough, under a 10 cm hydrostatic head, is at least 0.01 g/cm2/sec, where the flow rate is normalized by the area of fritted funnel 718. Factors particularly impactful on flow rate are the permeability of the fritted disc in fritted funnel 718 and the inner diameters of glass tubing 724, 730, 734, 742, 746 and 731a, and stopcock valves 728 and 740.

Reservoir 712 is positioned on an analytical balance 716 that is accurate to at least 0.01 g with a drift of less than 0.1 g/hr. The balance is preferably interfaced to a computer with software than can (i) monitor balance weight change at pre-set time intervals from the initiation of the PUP test and (ii) be set to auto initiate on a weight change of 0.01–0.05 g, depending on balance sensitivity. Capillary tubing 724 entering the reservoir 712 should not contact either the bottom thereof or cover 714. The volume of fluid (not shown) in reservoir 712 should be sufficient such that air is not drawn into capillary tubing 724 during the measurement. The fluid level in reservoir 712, at the initiation of the measurement, should be approximately 2 mm below the top surface of fritted disc in fritted funnel 718. This can be confirmed by placing a small drop of fluid on the fritted disc and gravimetrically monitoring its slow flow back into reservoir 712. This level should not change significantly when piston/cylinder assembly 720 is positioned within funnel 718. The reservoir should have a sufficiently large diameter (e.g., ~14 cm) so that withdrawal of ~40 ml portions results in a change in the fluid height of less than 3 mm.

Prior to measurement, the assembly is filled with Jayco synthetic urine. The fritted disc in fritted funnel 718 is forward flushed so that it is filled with fresh synthetic urine. To the extent possible, air bubbles are removed from the bottom surface of the fritted disc and the system that connects the funnel to the reservoir. The following procedures are carried out by sequential operation of the 3-way stopcocks:

1. Excess fluid on the upper surface of the fritted disc is removed (e.g. poured) from fritted funnel 718.
2. The solution height/weight of reservoir 712 is adjusted to the proper level/value.
3. Fritted funnel 718 is positioned at the correct height relative to reservoir 712.
4. Fritted funnel 718 is then covered with fritted funnel cover 722.
5. The reservoir 712 and fritted funnel 718 are equilibrated with valves 728 and 740 of stopcock assemblies 726 and 738 in the open connecting position.
6. Valves 728 and 740 are then closed.
7. Valve 740 is then turned so that the funnel is open to the drain tube 744.
8. The system is allowed to equilibrate in this position for 5 minutes.
9. Valve 740 is then returned to its closed position.

Steps Nos. 7–9 temporarily "dry" the surface of fritted funnel 718 by exposing it to a small hydrostatic suction of ~5 cm. This suction is applied if the open end of tube 744 extends ~5 cm below the level of the fritted disc in fritted funnel 718 and is filled with synthetic urine. Typically ~0.2 g of fluid is drained from the system during this procedure. This procedure prevents premature absorption of synthetic urine when piston/cylinder assembly 720 is positioned within fritted funnel 718. The quantity of fluid that drains from the fritted funnel in this procedure (called the fritted funnel correction weight) is measured by conducting the PUP test (see below) for a time period of 15 minutes without piston/cylinder assembly 720. Essentially all of the fluid drained from the fritted funnel by this procedure is very quickly reabsorbed by the funnel when the test is initiated. Thus, it is necessary to subtract this correction weight from weights of fluid removed from the reservoir during the PUP test (see below).

0.9 g of hydrogel-forming absorbent polymer 760 (corresponding to a basis weight of 0.032 g/cm2) is added to cylinder 754 and distributed evenly on screen 759. For most hydrogel-forming absorbent polymers, moisture content is typically less than 5%. For these polymers, the added polymer weight can be determined on a wet-weight (as it is) basis. For polymers having a moisture content greater than about 5%, the added polymer weight should be corrected for moisture (i.e., the added polymer should be 0.9 g on a dry-weight basis). Care is taken to prevent hydrogel-forming absorbent polymer 760 from adhering to the inside walls of cylinder 754. The piston 756 is slid into cylinder 754 and positioned on top of the hydrogel-forming absorbent polymer 760. The piston can be turned gently to help distribute the hydrogel-forming absorbent polymer. The piston/cylinder assembly 720 is placed on top of the frit portion of funnel 718, the weight 758 is slipped into piston 756, and the top of funnel 718 is then covered with fritted funnel cover 722. After the balance reading is checked for stability, the test is initiated by opening valves 728 and 740 so as to connect funnel 718 and reservoir 712. With auto initiation, data collection commences immediately, as funnel 718 begins to reabsorb fluid.

Data is recorded for a time period of 60 minutes.

Moisture content of the hydrogel-forming absorbent polymer is determined separately by measuring % weight loss after 3 hr @ $105_1$C. The measured moisture content is used to calculate the dry weight of hydrogel-forming polymer used in the PUP test.

$$\text{PUP capacity (gm/gm)}=[Wr(t=0)-Wr(t=60\ min)-Wfc]/\{Whfap; \text{dry-basis}\}$$

where Wr(t=0) is the weight in grams of reservoir 712 prior to initiation, Wr(t=60 min) is the weight in grams of reservoir 712 at 60 minutes, Wfc is the fritted funnel correction weight in grams (measured separately), and Whfap;dry basis is the dry weight in grams of the hydrogel-forming absorbent polymer.

What is claimed is:

1. Absorbent structure, comprising an ultimate fluid storage absorbent member, said ultimate fluid storage absorbent member having six surfaces: a top surface, a bottom surface, a front surface, a back surface and a pair of longitudinal side surfaces connecting said front and back surfaces and comprising superabsorbent material at a concentration of at least 40% of the total weight of said ultimate fluid storage absorbent member, said material having a Performance Under Pressure (PUP) value of at least 23 g/g, and a Saline Flow Conductivity (SFC) value of at least 30×10−7cm3sec/g, further comprising a non-woven wrap sheet comprising fibers having a fiber diameter corresponding to less than 1.2 dTex, said sheet is in direct fluid communication with said storage member, characterized in that said wrap sheet has a strike-through time in the second load of less than 60 seconds.

2. Absorbent structure according to claim 1, wherein said wrap sheet fibers have a dTex value of less than 0.9.

3. Absorbent structure according to claim 1, wherein said wrap sheet fibers have a dTex value of less than 0.7.

4. Absorbent structure according to claim 1, wherein said wrap-sheet comprises a melt-blown fibers.

5. Absorbent structure according to claim 1, wherein said wrap sheet has a strike-through time of less than 30 seconds.

6. Absorbent structure according to claim 1, wherein said wrap sheet has a strike-through time of less than 10 seconds.

7. Absorbent structure according to claim 1, wherein said wrap sheet has a strike-through time of less than 5 second.

8. Absorbent structure according to claim 1, wherein said superabsorbent material is present in more than about 50% concentration.

9. Absorbent structure according to claim 1, wherein said superabsorbent material is present in more than about 60% concentration.

10. Absorbent structure according to claim 1, wherein said superabsorbent material is present in more than about 70% concentration.

11. Absorbent structure according to claim 1, wherein said superabsorbent material is present in more than about 80% concentration.

12. Absorbent structure according to claim 1, wherein said superabsorbent material is present in more than about 90% concentration.

13. Absorbent structure according to claim 1 wherein said superabsorbent has a SFC value of at least 50×10−7cm3sec/g.

14. Absorbent structure according to claim 1 wherein said superabsorbent has a SFC value of at least 70×10−7cm3sec/g.

15. Absorbent structure according to claim 1 wherein said superabsorbent has a SFC value of at least 100×10−7cm3sec/g.

16. Absorbent structure according claim 1 wherein said superabsorbent has a PUP value of at least 27 g/g.

17. Absorbent structure according claim 1 wherein said superabsorbent has a PUP value of at least 29 g/g.

18. Absorbent article comprising an absorbent structure according to claim 1, wherein said wrap sheet completely envelops the absorbent member by being in direct contact with all of the six surfaces of the absorbent member.

19. Absorbent article comprising an absorbent structure according to claim 1, wherein said wrap sheet covers the top surface of the absorbent member, and is folded around the longitudinal side surfaces of the absorbent member.

20. Absorbent article according to claim 1, wherein said wrap sheet does not cover the complete bottom surface.

21. Absorbent article according to claim 1, further comprising a liquid impermeable backsheet positioned below the ultimate fluid storage absorbent member wherein the absorbent member is in direct contact with said backsheet.

22. Absorbent article according to claim 1, further comprising an acquisition member positioned between the wrap sheet and a topsheet.

23. Absorbent article according to claim 1, further comprising a fluid distribution member.

24. Absorbent article according to claim 1, being a baby or adult incontinence diaper.

* * * * *

UNITED STATES PATENT AND TRADEMARK OFFICE
CERTIFICATE OF CORRECTION

PATENT NO.    : 6,570,058 B1
DATED         : May 27, 2003
INVENTOR(S)   : Fuchs et al.

It is certified that error appears in the above-identified patent and that said Letters Patent is hereby corrected as shown below:

Column 11,
Line 54, please delete "11" and insert therefor -- II --.

Signed and Sealed this

Twenty-second Day of June, 2004

JON W. DUDAS
*Acting Director of the United States Patent and Trademark Office*